(12) United States Patent
Kimura et al.

(10) Patent No.: US 7,543,511 B2
(45) Date of Patent: Jun. 9, 2009

(54) CONCURRENTLY MEASURING A FORCE EXERTED UPON EACH OF A PLURALITY OF TEETH

(75) Inventors: Ryan Kimura, San Jose, CA (US); Heng Cao, Santa Clara, CA (US); Jon Moss, Anitoch, CA (US); Ken Wu, San Francisco, CA (US); Li-Hung Su, Foster City, CA (US)

(73) Assignee: Align Technology Inc., Santa Clara, CA (US)

( * ) Notice: Subject to any disclaimer, the term of this patent is extended or adjusted under 35 U.S.C. 154(b) by 3 days.

(21) Appl. No.: 11/881,529

(22) Filed: Jul. 27, 2007

(65) Prior Publication Data
US 2009/0030348 A1    Jan. 29, 2009

(51) Int. Cl.
*G01L 1/00* (2006.01)
(52) U.S. Cl. .................................. 73/862.381
(58) Field of Classification Search ............ 73/862.381, 73/778; 433/2, 24, 72
See application file for complete search history.

(56) References Cited

U.S. PATENT DOCUMENTS

| | | | |
|---|---|---|---|
| 4,549,555 A * | 10/1985 | Fraser et al. ................ 600/595 |
| 5,630,717 A | 5/1997 | Zuest et al. |
| 5,791,350 A | 8/1998 | Morton |
| 5,885,078 A | 3/1999 | Cagna et al. |
| 6,120,287 A * | 9/2000 | Chen .............................. 433/2 |
| 2007/0065768 A1 * | 3/2007 | Nadav .......................... 433/6 |

OTHER PUBLICATIONS

Cao, Heng et al., "Applications of Mechanics with Invisalign", *The Invisalign System,Quintessence Publishing Company*, (2006),153-161.

* cited by examiner

*Primary Examiner*—Jewel Thompson

(57) ABSTRACT

A system and method for concurrently measuring a force exerted upon a tooth is disclosed. In one aspect of the invention, the system includes a target tooth attached to a force gauge which is coupled to a motion module for adjusting the tooth to a reference position. The method includes utilizing a motion module of a force measurement device is utilized to adjust each target tooth of a plurality of target teeth to be located in a reference position. Next, each target tooth receives a dental appliance. Then an exerted force is measured by the dental appliance upon each target tooth utilizing a coordinate system of the force gauge.

19 Claims, 4 Drawing Sheets

CONCURRENTLY MEASURING A FORCE EXERTED UPON EACH OF A PLURALITY OF TEETH

FIELD OF THE INVENTION

The present invention relates generally to the field of orthodontics.

BACKGROUND OF THE INVENTION

Orthodontic treatments involve repositioning misaligned teeth and improving bite configurations for improved cosmetic appearance and dental function. Repositioning is typically accomplished by a dentist or orthodontist (hereinafter practitioner) applying gentle forces by a dental appliance (e.g., braces or positioning appliances) to a patient's teeth over an extended period of time. Due to the limited space within the oral cavity and extensive movements that some teeth must undergo, the teeth will often be moved throughout a series of intermediate patterns to properly arrange the teeth.

Braces comprise a variety of appliances such as brackets, bands, archwires, ligatures, and O-rings. After the brackets are bonded to the teeth, periodic meetings with the treating practitioner are required to allow them to reactively adjust the braces. This generally involves crimping existing archwires or installing new archwires having different force-inducing properties, and/or replacing or tightening existing ligatures.

In contrast, positioning appliances or aligners are comprised of a thin shell of material that generally conforms to a patient's teeth but each appliance provides a teeth receiving cavity geometry that is slightly out of alignment with the initial tooth configuration. Placement of the aligner over the teeth applies controlled forces in specific locations to gradually move the teeth into a new configuration of a predetermined treatment plan. Repetition of this process with successive aligners, each providing a new unique teeth receiving cavity, eventually moves the teeth through a series of intermediate arrangements to a final desired arrangement in accordance with the predetermined treatment plan.

The force that will be generated by braces or an aligner system to teeth can be calculated by finite element analysis modeling. Currently, the systems that exist for obtaining such measurements suffer from issues of inaccuracy and their ability to look at multiple teeth and their movements relative to each other. Thus, it takes much time and effort to obtain a force measurement for multiple teeth within the jaw structure, and any result can rarely be replicated.

SUMMARY

A method for concurrently measuring a force exerted upon each of a plurality of teeth is disclosed. Initially, a motion module of a force measurement device is utilized to adjust each target tooth of a plurality of target teeth to be located in a reference position. Then, each target tooth receives a dental appliance. Then the present technology measures a force exerted by the dental appliance upon each target tooth utilizing a coordinate system of the force gauge.

Figure 1:
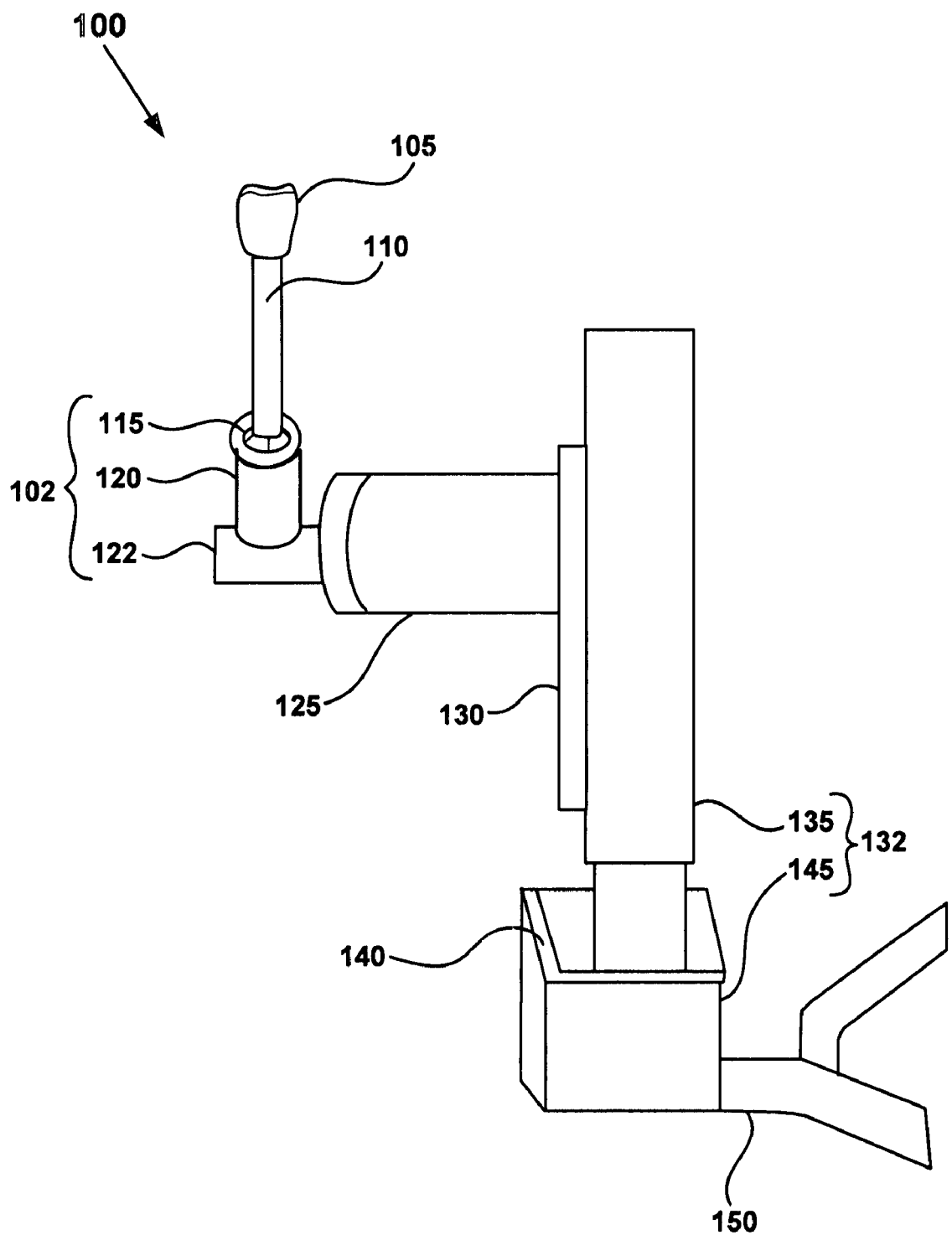
FIG. 1 is a perspective view of a force measurement device, according to one embodiment of the present technology.

The drawings referred to in this description should not be understood as being drawn to scale unless specifically noted.

DETAILED DESCRIPTION OF THE INVENTION

Before the present force measurement device, force measurement systems and methods are described, it is to be understood that this invention is not limited to particular tools, systems and methods specifically described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described.

It must be noted that as used herein and in the appended claims, the singular forms "a", "an", and "the" include plural referents unless the context clearly dictates otherwise. Thus, for example, reference to "a tooth" includes a plurality of such teeth, and reference to "the appliance" includes reference to one or more appliances and equivalents thereof known to those skilled in the art, and so forth.

While specific reference may be made to a user, patient, practitioner, or other person using the disclosed tools and systems, and practicing the disclosed methods, it is to be understood that such terms are meant to be inclusive of all such users, unless the context clearly dictates otherwise.

The discussion will begin with an overview of the general process of considering magnitude and direction of forces generated by aligners to facilitate treatment, and the limitations of this process. The discussion will then focus on embodiments of the present technology that provide a force measurement device for measuring a force exerted upon a target tooth assembly, and that provide a force measurement system for concurrently measuring a force exerted upon a target tooth of each of a plurality of target tooth assemblies. The discussion will then focus on the method for concurrently measuring a force exerted upon a target tooth of each of a plurality of target tooth assemblies.

Overview

Aligners are fabricated at each treatment stage using treatment software that redefines each tooth as a solid three dimensional crown object. Due to the particular materials and processes used in manufacturing aligners, the aligner thicknesses are not uniform. Depending upon tooth shape, size, height, and location, and aligner material used, the wall thickness of the aligner can vary. For example, short fat molars may have thicker aligner shells, while tall thin incisors may have thinner aligner shells. These uneven wall thicknesses may cause each tooth to experience a different level of force exerted by an aligner. Additionally, in general, it is difficult to consider the magnitude and direction of the force and torque that a treatment aligner will deliver on a particular tooth.

Embodiments of the present technology provide a method for concurrently measuring a force exerted by a dental appliance (e.g., braces or aligner) upon each target tooth of a plurality of target teeth. For example, a target tooth is coupled to a motion module via a force gauge. After an initialization tool is placed over the target tooth as well as the cut jaw, the motion module utilizes its six degrees of freedom of movement to adjust the target tooth until a force gauge confirms that the initialization tool is no longer exerting force upon the target tooth. Once a zero state force is indicated, then the initialization tool is removed.

A treatment aligner representing an (N+1) treatment stage is then placed over the target tooth and the cut jaw from treatment stage N, thereby again exerting a force upon each target tooth. Utilizing the force gauge and its coordinate system, the six components of force exerted upon the target tooth of each of the plurality of target teeth is then measured. (x, y, z, a, b, and c, wherein a, b, and c represent the torques about the X, Y, and Z axes respectively).

By measuring a force exerted upon a target tooth utilizing the force gauge's coordinate system, the force exerted upon each target tooth of a plurality of target teeth may be concurrently measured. In this manner, the present technology is capable of capturing the differences in force exerted upon each target tooth by aligners with uneven wall thicknesses. Additionally, this force measurement device will determine how much force is being applied to a particular tooth by a dental appliance.

The following discussion will begin with a description of the structure of the components of the present technology. This discussion will then be followed by a description of the components in operation.

Structure

With reference now FIG. 1, a perspective view of a force measurement device 100 is shown for translating forces to a sensor that are applied to a target tooth 105. In this embodiment, force measurement device 100 includes force translation assembly 102, force gauge 125, and motion module 132. More specifically, force translation assembly includes collet 115, nut 120, and first adapter 122. Motion module 132 includes vertical slider 135 and a set of two goniometers enclosed within a goniometer casing 145. Force translation assembly 102 is coupled to force gauge 125, which itself is coupled to motion module 132. Vertical slider 135 is coupled to force gauge 125 by second adapter 130. Vertical slider 135 is coupled to goniometer casing 145 by third adapter 140. Additionally, target tooth 105, support rod 110, and base plate 150 are shown.

Figure 2:
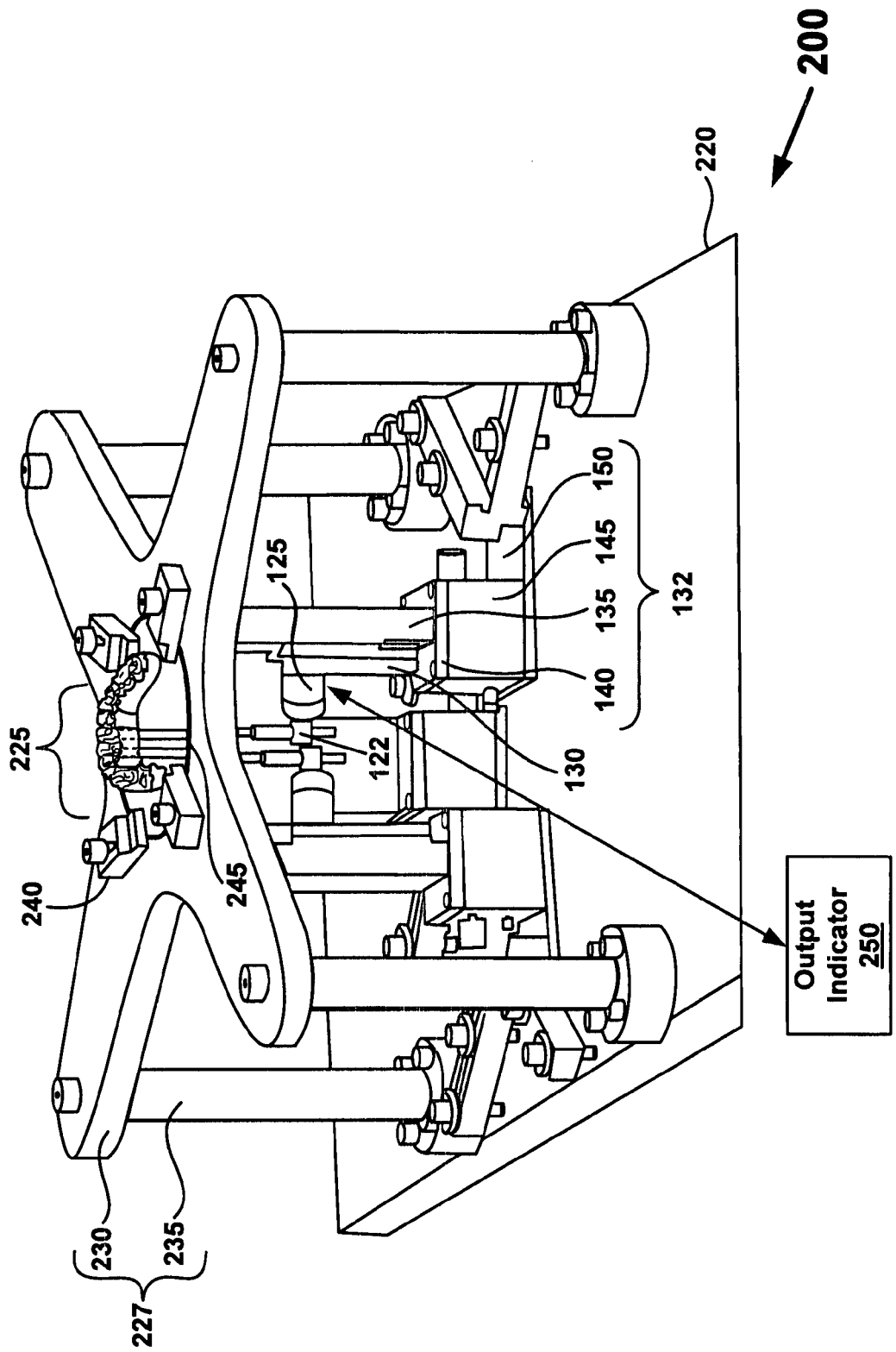
FIG. 2 is a perspective view of a system for concurrently measuring a force exerted upon each of a plurality of teeth, according to one embodiment of the present technology.

With reference now to FIG. 2, a perspective view of a system 200 for concurrently measuring a force exerted upon each of a plurality of teeth by a dental appliance is shown. In this embodiment, system 200 includes force gauge 125 coupled to motion module 132 by second adapter 130. Motion module 132 includes vertical slider 135, third adapter 140, goniometer casing 145, and base plate 150 coupled to base board 220. Frame 227 includes platform 230 and posts 235, and is coupled to base board 220. Also shown as associated with platform 230 are cut jaw 225, clamps 240, and opening 245.

The above assembled components enable force measurement device 100 to measure a force exerted upon target tooth 105. For example, a three dimensional model of target tooth 105 is made. Target tooth 105 is coupled to support rod 110. Support rod 110 is coupled to force gauge 125 by first adapter 122. In particular, support rod 110 is inserted into a hole within first adapter 122, and locked into place by the tightening of a clamping assembly, such as a nut 120 around collet 115. Initialization tool 300 (FIG. 3), representing reference stage N of target tooth 105, is placed over target tooth 105. A force is exerted upon target tooth 105. This force is transmitted through support rod 110 to force gauge 125. Force gauge 125 measures the force exerted upon target tooth 105 to be at a non-zero state since target tooth 105 is experiencing the application of pressure from initialization tool 300. The components of motion module 132 are then re-positioned in any combination of the six directions, x, y, z, a, b, and c (wherein a, b, and c are torques about the X, Y, and Z axes, respectively), thereby re-positioning target tooth 105, until a zero state of force is recorded by force gauge 125.

A treatment aligner, representing the target placement N+1 of tooth 105, is then applied to target tooth 105 arranged within cut jaw 225, thereby once again applying pressure to target tooth 105. Force gauge 125 measures the force exerted upon target tooth 105 and records this measurement within its force gauge 125 coordinate system. This recorded measurement is then sent to output indicator 250 for conversion to a point-of-contact coordinate system. Consequently, in one embodiment, force measurement device 100, as will be described in greater detail in the Operation section herein, enables the measurement of force as exerted by an aligner onto a target tooth in the x, y, z, a, b, and c directions.

Target tooth 105 is a three dimensional model of a person's tooth. Target tooth 105 is created in any manner within the state of the art of forming three dimensional models of objects. In one example, target tooth 105 is configured to be arranged within cut jaw 225. In another example, target tooth 105 is made of metal, such as aluminum, stainless steel, and the like.

Support rod 110 is an object which is longer than it is wide. Support rod 110 is configured to be received at its first end by force translation assembly 102. The second end of support rod 110 is configured to be coupled to target tooth 105. Additionally, in one embodiment support rod 110 is also made of metal, such as aluminum, stainless steel, and the like. Target tooth 105 may be coupled to support rod 110 in a number of ways such as: a threader hole in target tooth 105 that receives a thread in the end of support rod 110, glue between target tooth 105 and support rod 110, single body construction, cotter-pin structure, and the like.

Force translation assembly 102 is configured for transferring forces acting upon target tooth 105 to force gauge 125 such that these forces can be quantitatively measured. Force translation assembly includes collet 115, nut 120, and first adapter 122 coupled to force gauge 125. In one embodiment, force translation assembly 102 is configured to receive a first end of support rod 110.

Collet 115 is configured to lock said support rod 110 into place by tightening nut 120 around collet 115. In one embodiment, collet 115 and nut 120 are made of metal, such as aluminum, stainless steel, and the like. However, collet 115 and nut 120 may be made of any material which allows the present technology to operate in the manner described herein. It should be appreciated that any clamping assembly may be used to lock support rod 110 into place.

Force gauge 125 is configured to measure the force exerted upon target tooth assembly 101. An example of force gauge 125 suitable for use in the present technology is sold under the trademark Nano 17 Sensor™, and are available for purchase from companies such as ATI Industrial Automation, located at Pinnacle Park, 1031 Goodworth Drive, Apex, N.C. 27539. However, other force gauges 125 suitable for use in the present technology may be used. In one embodiment, force gauge 250 is oriented horizontally. In another embodiment, force gauge is configured to receive a metal tooth as a target tooth 105.

Motion module 132 includes vertical slider 135 coupled to goniometer casing 145 by third adapter 140. In one embodiment, motion module 132 also includes base plate 150. In one example of the present technology, motion module 132 exhibits four degrees of freedom of movement (a, b, c, and z). In another example, motion module 132 exhibits six degrees of freedom of movement (a, b, c, x, y, and z). Vertical slider 135 is coupled to force gauge 125 by second adapter 130, and is configured to move up and down in the vertical direction, thereby also moving force gauge 125 and target tooth assembly 102 in the vertical direction. Goniometer casing 145 encloses two goniometers which are configured to enable angular adjustment of said target tooth assembly. In one embodiment, goniometer casing 145 is coupled to base board 220 directly, while in another embodiment, goniometer casing 145 is coupled to base plate 150, which base plate 150 is then coupled to base board 220.

Frame 227 is coupled to base board 220 and is configured to secure cut jaw 225 proximate the force measurement devices 100. In one embodiment, frame 227 includes platform 230 and posts 235. Platform 230, having opening 225 within its structure, is coupled to base board 220 by a plurality of posts 235. Clamps 240 couple cut jaw 225 to platform 245, so that cut jaw 225 is held into place within opening 245.

Platform 230 is configured to be elevated above base board 220 such that there is sufficient space under cut jaw 225 for maneuvering each of the plurality of force measurement devices 100. In one embodiment, a plurality of posts 235 are configured to raise platform 230 up and off of base board 220. It should be appreciated that platform 230 may be elevated by any number of objects which would elevate platform 230 to provide sufficient space to maneuver force measurement devices 100, such as a wall, beams, balls, and the like. Sufficient space is that space which would allow force measurement device 100 to be adjusted and/or operated.

Cut jaw 225 is a three dimensional model of a partial set of teeth within a jaw. For example, the lower jaw may have 16 teeth, wherein only 13 are represented in cut jaw 225. In one embodiment, cut jaw 225 is also made of metal, such as aluminum, stainless steel, and the like. Target teeth 105 arranged within cut jaw 225 may be positioned adjacent to one another and/or be spaced separately from one another.

Opening 245 is configured to enable cut jaw to be oriented therein. In one embodiment, opening 245 is centered within platform 230. In another embodiment, opening 245 is off-center within platform 230. Additionally, opening 245 may be any shape, such as round, square, rectangular, and the like.

Output indicator 250 is communicatively coupled to force gauge 125 (either wired or wirelessly) and is configured to convert the force coordinate measurements of force gauge 125 into a tooth's point-of-contact coordinate system as well as display the results. Output indicator 250 may be integral within the structure of force measurement device 100 or may be separately located.

Figure 3:
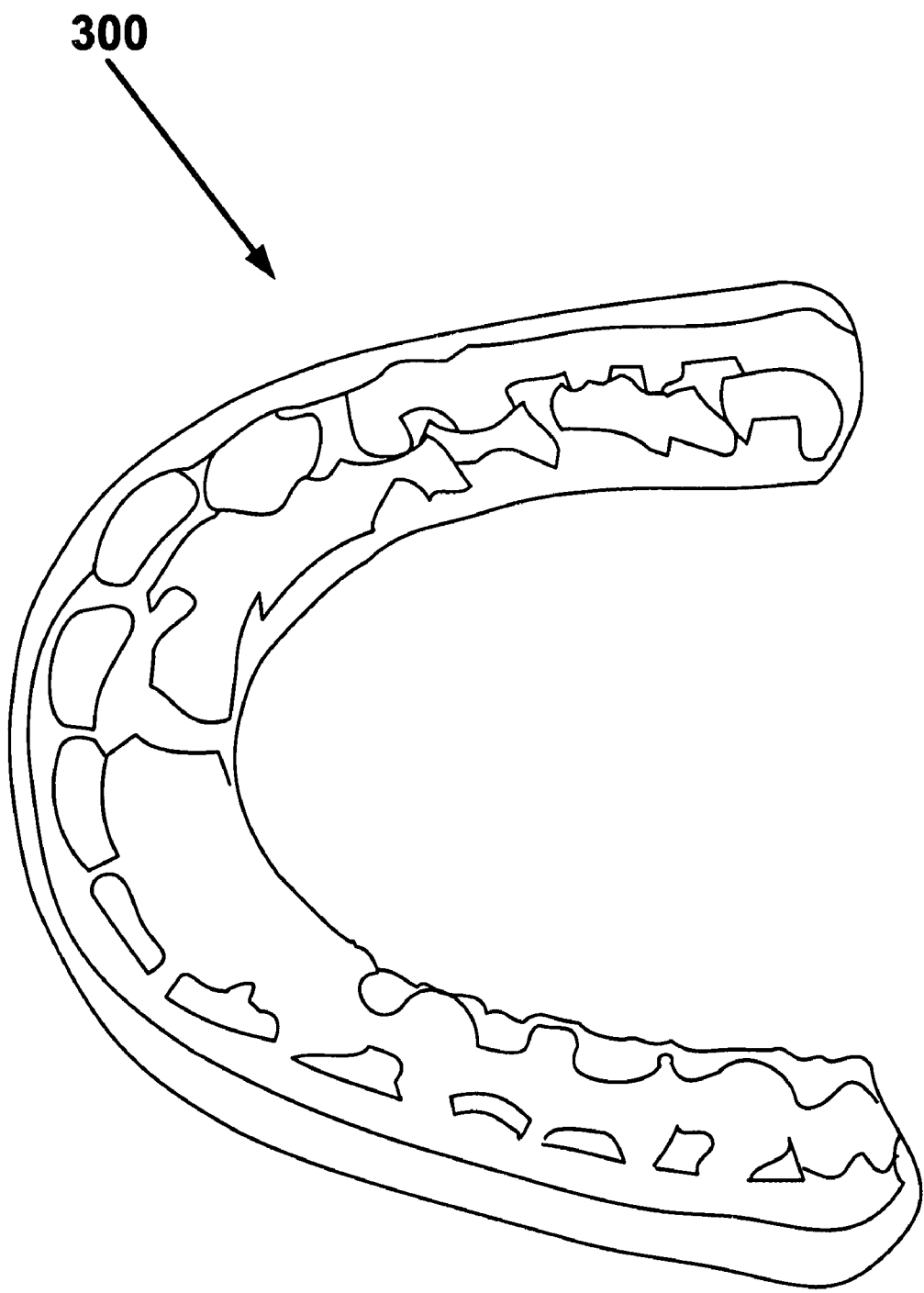
FIG. 3 is a perspective view of an initialization tool, according to one embodiment of the present technology.

With reference now to FIG. 3, a perspective view of an initialization tool 300 is shown. Initialization tool 300 is configured to locate a target tooth 105 or a plurality of target teeth 105 to a reference position.

The dental appliance may be, but is not limited to the following: an initialization tool, a test aligner, and braces. Using techniques known in the state of the art of orthodontics, an initialization tool is made from a mold, which mold was formed based upon an original digital model of a set of teeth. The initialization tool is used to fit over a set of teeth (either a three dimensional model or a person's set of teeth), and to realign this set of teeth so that they match the original digital model of a set of teeth (considered to be the reference position).

For example, a model of each crown of a set of teeth is formed. Each resulting crown model is then aligned to be in a position matching its corresponding position within a set of teeth. An initialization tool is placed over the aligned crown models. The aligned crown models are then repositioned so as to fit within their corresponding cavity within the initialization tool. Consequently, the initialization tool is used to reposition crown models of a set of teeth so that the set of crown models replicate the positioning of the set of teeth and hence create a reference position.

A treatment aligner is a variation of the initialization tool described herein, and is formed based upon the original digital model of a set of teeth. However, the treatment aligner represents a mold which is designed to fit a set of teeth (either a three dimensional model or a person's set of teeth) in such a way as to realign the set of teeth to the targeted position of the cavities spaces within the treatment aligner.

Operation

Figure 4:
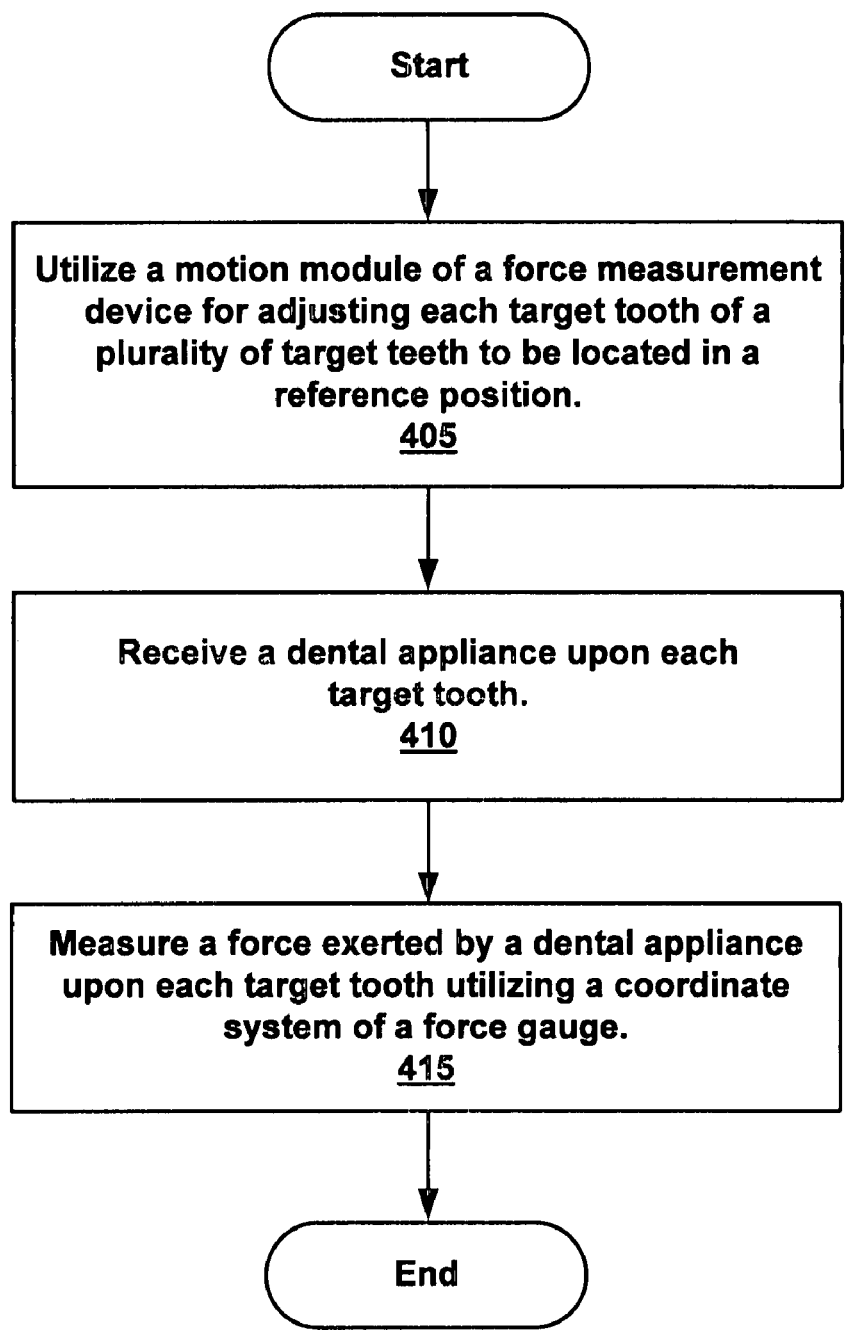
FIG. 4 is a flow diagram of an example method for concurrently measuring a force exerted upon each of a plurality of teeth, according to one embodiment of the present technology.

Turning now to FIG. 4, a flow diagram 400 is shown of an example method for concurrently measuring a force exerted upon each of a plurality of teeth by a dental appliance. With reference to FIGS. 1-3, step 405 recites how motion module 132 of force measurement device 100 is utilized for adjusting each target tooth 105 of a plurality of target teeth 105 to be located in a reference position.

Initially, in one embodiment, target tooth 105 is placed within a cavity of cut jaw 225, wherein cut jaw 225 is coupled to platform 230. In another embodiment, a plurality of target teeth 105 are placed within cavities of cut jaw 225. Hereinafter, discussions referring to target tooth 105 may also reference a target tooth 105 to be in a plurality, unless otherwise noted. Then, initialization tool 300 representing a desired reference position is placed over target teeth 105 and cut jaw 225, exerting a force upon each target tooth 105. Motion module 132 is then manipulated in order to adjust target tooth 105 such that target tooth 105 is no longer experiencing a force (at zero state).

In one embodiment, motion module 132 may be adjusted in four different directions. In another embodiment, motion module 132 may be adjusted in six different directions. For example, by adjusting vertical slider 135 of motion modules 132 upward, target tooth 105 is also vertically adjusted. This is because target tooth 105 is operatively coupled to vertical slider 135, as described herein. Hence, a movement made by motion module 132 is experienced by target tooth 105. It is appreciated that tooth 105 and support rod 110 may be moved vertically and/or rotated inside of collet 115 and adapter 122 before being locked into place by tightening nut 120 around collet 115.

In one embodiment, target tooth 105 may also be adjusted angularly (along the a, b, and c, rotational directions) through the use of two goniometers within goniometer casing 145. Additionally, goniometer casing 145 may be slid horizontally (along the x axis) along base board 220 and then fixed into place. In another embodiment, base plate 150 which is coupling goniometer casing 145 to base board 220, may be slid in the horizontal plane along base board 220, and then fixed into place.

While adjusting target tooth 105 with motion module 132, force gauge 125 of force measurement device 100 utilizes a coordinate system to provide a real-time measurement of the force which initialization tool 300 is exerting upon target tooth 105. Once this measurement indicates a zero state of force exerted upon each target tooth 105, then a reference position has been located. In other words, initialization tool 300 is utilized to calibrate each target tooth 105 to a zero state force. In response to the reference position being located, support rod 110 is locked into place by force translation assembly 102.

Referring again to FIG. 4, as well as to FIGS. 1-3, step 410 provides for receiving a dental appliance upon each target tooth 105. For example, a treatment aligner is placed upon each target tooth 105 arranged within cut jaw 225, having already been located in a reference position. A force is once again being exerted upon each target tooth 105, this time by the treatment aligner.

At step 415, the present technology provides for measuring a force exerted by a dental appliance upon each target tooth 105 utilizing a coordinate system of force gauge 125. For example, the force exerted upon each target tooth 105 by a treatment aligner may be measured by force gauge 125 in a similar manner in which force gauge measured the force exerted by initialization tool 300.

In one embodiment, the present technology stores this measurement within a data logger of force gauge 125. In another embodiment, the present technology converts the stored measurement from a coordinate system of force gauge 125 to a point-of-contact coordinate system for target tooth 105.

For example, in one embodiment, the stored measurements are pulled from a data logger within force gauge 125, and then formatted into a spreadsheet. To aid in data analysis and to reduce any background noise created by initialization tool 300, an automated triggering script is utilized to locate the initial reference start point of the test. Next, a script using a transformation matrix converts the force and torque values from the coordinate system of force gauge 125 to the point-of-contact coordinate system of each target tooth 105.

To obtain the transformation matrix, measurements are conducted to obtain information regarding the difference between coordinate system of force gauge 125 and the coordinate system of each target tooth 105. This measurement may be conducted in Computer Assisted Design (CAD) software, since each part of a real apparatus has a CAD counterpart. The measurement may also be conducted by imaging techniques based on photogrammetry algorithms.

Additionally, in one embodiment, due to the structure and composition of the present technology, force measurement device 100 may be turned upside down so that target tooth 105 and part of support rod 110 are placed in a bath of heated artificial saliva to simulate the wet, warm, and humid oral environment that a dental appliance must endure during extended patient wear. By enabling target tooth 105 to be dipped into a bath of heated artificial saliva, the force exerted upon each target tooth 105 may be measured during a more realistic enactment of factors affecting orthodontic treatment.

The present technology is also well suited to studying the effects of force and torques that an aligner applies on target tooth 105 before, during, and after aligner distortions occur from occlusion with the mating jaw, while being immersed in heated artificial saliva. For example, a model of a lower jaw may already be immersed in heated artificial saliva. Its mating jaw, coupled to force measurement device 100, may then be turned upside down so that target tooth 105 and part of support rod 110 are also placed in the bath of heated artificial saliva such that target tooth 105 of the mating jaw interconnects with the lower jaw. The force exerted upon target tooth 105 is then calculated. In this manner, an understanding will be gained of how aligner distortion from biting and/or being subjected to a heated and wet environment will affect the force and torque related to tooth movement.

In calculating the force exerted upon target tooth 105 by a dental appliance using the disclosed force measurement device 100, it is possible to concurrently determine the force exerted upon a plurality of target teeth 105. Additionally, the present technology enables the determination of a force a treatment aligner delivers to each target tooth 105.

All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A force measurement device comprising:
   a force gauge, said force gauge configured for measuring a force exerted upon a target tooth coupled to said force gauge;
   a motion module coupled to said force gauge, said motion module configured for adjusting said target tooth to a reference position; and
   a force translation assembly coupled to said force gauge, said force translation assembly configured for transferring forces acting upon said target tooth to said force gauge such that said forces can be quantitatively measured and wherein said force translation assembly is configured to receive a first end of a support rod, wherein said second end of said support rod is configured for being coupled to said target tooth.

2. The force measurement device of claim 1 wherein a coupling method by which said second end of said support rod is configured for being coupled to said target tooth is selected from a group of coupling methods consisting of: threading, gluing, single body construction, and cotter-pin structure.

3. The force measurement device of claim 1 wherein said force translation assembly is configured to receive a first end of a support rod, wherein said support rod is comprised of metal.

4. The force measurement device of claim 1, wherein said force measurement device is configured to receive a metal tooth as said target tooth.

5. The force measurement device of claim 1, wherein said force gauge is oriented horizontally.

6. The force measurement device of claim 1, wherein said motion module comprises:
   a vertical slider coupled to said force gauge, said vertical slider configured to enable vertical adjustment of said target tooth; and
   a plurality of goniometers coupled to said vertical slider and to said base board, each of said plurality of goniometers configured to enable angular adjustment of said target tooth.

7. The force measurement device of claim 6, further comprising:
   a base plate configured to couple said each of said plurality of goniometers to said base board.

8. The force measurement device of claim 1, wherein said motion module is configured to exhibit four degrees of freedom of movement.

9. The force measurement device of claim 1, wherein said motion module is configured to exhibit six degrees of freedom of movement.

10. The force measurement device of claim 1, wherein said target tooth is configured to be arranged within a cut jaw.

11. A system for concurrently measuring a force exerted upon each of a plurality of teeth, said system comprising:
a base board;
a plurality of force measurement devices coupled to said base board, each of said plurality of force measurement devices comprising:
a force gauge, said force gauge configured for measuring a force exerted upon a target tooth coupled to said force gauge; and
a motion module coupled to said force gauge, said motion module configured for adjusting said target tooth to a reference position;
a frame coupled to said base board, wherein said frame is configured to secure a cut jaw proximate said force measurement devices, said cut jaw configured to receive at least one target tooth therein; and
an output indicator coupled to a plurality of said force gauges, said output indicator configured to provide a measure of force exerted on said at least one target tooth.

12. The system of claim 11, wherein said frame comprises:
a platform coupled to said cut jaw, wherein said platform has an opening within which said cut jaw is oriented, said platform configured to be elevated above said base board such that there is sufficient space under said cut jaw for maneuvering each of said plurality of force measurement devices.

13. The system of claim 11, wherein said motion module is configured to exhibit six degrees of freedom of movement.

14. A method for concurrently measuring a force exerted upon each of a plurality of teeth by a dental appliance, said method comprising:
utilizing a motion module of a force measurement device for adjusting each target tooth of a plurality of target teeth to be located in a reference position;
receiving a dental appliance upon said each said target tooth; and
measuring a force exerted by said dental appliance upon said each said target tooth utilizing a coordinate system of said force gauge.

15. The method as recited in claim 14, wherein said adjusting each target tooth of a plurality of target teeth to be located in a reference position further comprises:
calibrating said each said target tooth to a zero state force by utilizing an initialization tool.

16. The method as recited in claim 14, further comprising:
storing said measurement within said force gauge.

17. The method as recited in claim 14, further comprising:
converting said stored measurement from a coordinate system of said force gauge to a point-of-contact coordinate system for said target tooth.

18. The method as recited in claim 14, further comprising:
exhibiting by said motion module four degrees of freedom of movement.

19. The method as recited in claim 14, further comprising:
exhibiting by said motion module six degrees of freedom of movement.

* * * * *